US010251411B2

(12) United States Patent
Summer

(10) Patent No.: US 10,251,411 B2
(45) Date of Patent: Apr. 9, 2019

(54) PROTEIN-RICH FEEDSTUFF WITH RESISTANCE TO LOWERED DIGESTIBILITY DUE TO HEAT DAMAGE

(71) Applicant: AJINOMOTO NORTH AMERICA, INC., Fort Lee, NJ (US)

(72) Inventor: Paul Summer, Fort Lee, NJ (US)

(73) Assignee: AJINOMOTO NORTH AMERICA, INC., Fort Lee, NJ (US)

( * ) Notice: Subject to any disclaimer, the term of this patent is extended or adjusted under 35 U.S.C. 154(b) by 930 days.

(21) Appl. No.: 14/562,962

(22) Filed: Dec. 8, 2014

(65) Prior Publication Data

US 2015/0093474 A1 Apr. 2, 2015

Related U.S. Application Data

(60) Division of application No. 12/885,867, filed on Sep. 20, 2010, now abandoned, which is a continuation of application No. PCT/JP2009/001202, filed on Mar. 18, 2009.

(60) Provisional application No. 61/038,563, filed on Mar. 21, 2008, provisional application No. 61/079,243, filed on Jul. 9, 2008.

(51) Int. Cl.
| | |
|---|---|
| *A23K 20/105* | (2016.01) |
| *A61K 31/205* | (2006.01) |
| *A23K 10/38* | (2016.01) |
| *A23K 10/30* | (2016.01) |
| *A23K 20/147* | (2016.01) |
| *A23K 20/142* | (2016.01) |
| *A23K 50/10* | (2016.01) |

(52) U.S. Cl.
CPC .......... *A23K 20/105* (2016.05); *A23K 10/30* (2016.05); *A23K 10/38* (2016.05); *A23K 20/142* (2016.05); *A23K 20/147* (2016.05); *A23K 50/10* (2016.05); *A61K 31/205* (2013.01); *Y02P 60/873* (2015.11); *Y02P 60/877* (2015.11)

(58) Field of Classification Search
CPC .... A23K 20/142; A23K 20/147; A23K 50/10; A23K 10/30; A61K 31/205; Y02P 60/873; Y02P 60/877
See application file for complete search history.

(56) References Cited

U.S. PATENT DOCUMENTS

| | | | |
|---|---|---|---|
| 2,535,117 A | 12/1950 | Bennett | |
| RE24,707 E | 9/1959 | Gillis | |
| 3,463,858 A | 8/1969 | Anderson | |
| 5,177,009 A | 1/1993 | Kampen | |
| 5,709,894 A | 1/1998 | Julien | |
| 5,760,078 A | 6/1998 | Hamstra et al. | |
| 5,773,052 A | 6/1998 | Virtanen et al. | |
| 6,183,769 B1 | 2/2001 | Campbell et al. | |
| 6,387,419 B1 | 5/2002 | Christensen | |
| 6,514,521 B1 | 2/2003 | Julien | |
| 6,709,481 B2 | 3/2004 | Julien | |
| 6,858,239 B2 | 2/2005 | Julien | |
| 6,962,722 B2 | 11/2005 | Dawley et al. | |
| 2003/0123961 A1* | 7/2003 | Lewis | B61D 9/00 414/354 |
| 2003/0180415 A1 | 9/2003 | Stiefel et al. | |
| 2004/0185148 A1 | 9/2004 | Said | |
| 2005/0255145 A1* | 11/2005 | Macgregor | A23K 40/35 424/438 |
| 2006/0204554 A1 | 9/2006 | Cecava et al. | |
| 2007/0225514 A1* | 9/2007 | Davis | C11B 1/104 554/9 |
| 2008/0152755 A1* | 6/2008 | Lebo | A23K 40/00 426/2 |

FOREIGN PATENT DOCUMENTS

| | | |
|---|---|---|
| BR | 9301144 A | 1/1994 |
| FR | 2 788 407 A1 | 7/2000 |
| JP | 60-17502 | 5/1985 |
| JP | 7-4170 | 1/1995 |
| JP | 11-18692 | 1/1999 |
| JP | 3495429 | 2/2004 |
| SU | 438407 A | 1/1975 |
| SU | 586889 A | 1/1978 |
| WO | 96/32850 | 10/1996 |

OTHER PUBLICATIONS

Arakawa et al. Biophys. J, vol. 47, Mar. 1985, pp. 411-414.*
Santoro et al. Biochemistry, 1992, 31, pp. 5278-5283.*
"Distiller's Grains Feeding Recommendations" downloaded from www.cie.us/documents/111005DGFRBeef.pdf, dated May 19, 2004, 24 pages.*
International Preliminary Report on Patentability dated Sep. 21, 2010 and Written Opinion of the International Searching Authority dated Mar. 18, 2009 in International Application No. PCT/JP2009/001202, International Filing Date Mar. 18, 2009.
International Search Report dated Jun. 30, 2009 in International Application No. PCT/JP2009/001202, International Filing Date Mar. 18, 2009.
Extended European Search Report dated Feb. 25, 2011, in European Patent Application No. 09722524.7-2114.
Database Biosis [Online], Database Accession No. PREV200100370429, XP-002622557, vol. 198, No. 3-4, Jul. 2, 2001, 1 page.
K. C. Klasing, et al., "Dietary Betaine Increases Intraepithelial Lymphocytes in the Duodenum of Coccidia-Infected Chicks and Increases Functional Properties of Phagocytes", Journal of Nutrition, Wistar Institute of Anatomy and Biology, vol. 132, No. 8, XP-008069768, Jan. 1, 2002, pp. 2274-2282.
T. Nakamura, et al., "Growth Efficiency and Digestibility of Heated Protein Fed to Growing Ruminants", J. Anim. Sci. vol. 72, 1994, pp. 774-782.

(Continued)

Primary Examiner — C. Sayala
(74) Attorney, Agent, or Firm — Oblon, McClelland, Maier & Neustadt, L.L.P.

(57) ABSTRACT

Protein-rich feedstuffs which contain at least one protein feed material and either betaine or at least one feed product which contains betaine are resistant to reduction of digestibility as a result of heat damage during drying.

19 Claims, No Drawings

(56) References Cited

OTHER PUBLICATIONS

D. H. Kleinschmit, et al., "Ruminal and Intestinal Degradability of Distillers Grains plus Solubles Varies by Source", J. Dairy Sci., vol. 90, 2007, pp. 2909-2918.
Stuart AS Craig, Betaine in Human Nutrition[1,2n], Review Article, Am. J. Clin. Nutr., vol. 80, 2004, pp. 539-549.
"Nutrient Requirements of Beef Cattle", Seventh Revised Edition, National Academy Press 1996, 5 pages.
"Nutrient Requirements of swine", published by National Academy Press, Wash D.C. 1988, Sixth Edition, p. 50.
Koeleman, Feed Tech, dated Mar. 2006, pp. 22-23, www.AgriWorld.nl.
Fernandez et al. Anim. Feed Sci & Tech, vol. 86, (2000) pp. 71-82.
Loest et al. Cattleman's Day 1998, pp. 76-78.
Fernandez-Figares et al. J. Anim. Sci 2008, vol. 86, pp. 102-111.
Pioneer Hi Bread, downloaded from www.pioneer.com, dated Oct. 10, 20035 pages.
J. Mauron, J. Nutr. Sci.Vitaminol., vol. 36, pp. S57-S69 (1990).
D.H. Kleinschmit et al., J. Dairy Sci., vol. 90, pp. 2909-2918 (2006).
F. N. Almeida et al., J. Anim. Sci. and Biotech., vol. 4, pp. 44-53 (2013).

\* cited by examiner

PROTEIN-RICH FEEDSTUFF WITH RESISTANCE TO LOWERED DIGESTIBILITY DUE TO HEAT DAMAGE

CROSS-REFERENCE TO RELATED APPLICATIONS

This application is a divisional of and claims priority to U.S. application Ser. No. 12/885,867, filed Sep. 20, 2010, now abandoned, the disclosure of which is incorporated herein by reference in its entirety. U.S. application Ser. No. 12/885,867 is a continuation of and claims priority to International Application No. PCT/JP2009/001202, filed Mar. 18, 2009, the disclosure of which is incorporated herein by reference in its entirety. This application claims priority to U.S. Provisional Patent Applications No. 61/038,563, filed Mar. 21, 2008, and No. 61/079,243, filed Jul. 9, 2008, the disclosures of which are incorporated herein by reference in their entireties.

TECHNICAL FIELD

The present invention relates to protein-rich feedstuffs. In particular, the present invention relates to protein-rich feedstuffs which are resistant to reduction of digestibility as a result of heat damage during drying. The present invention also relates to processes for making such feedstuffs. The present invention further relates to processes for raising livestock by feeding livestock such a protein-rich feedstuff. The present invention also relates to processes for making meat by harvesting meat from livestock which have been fed such a protein-rich feedstuff. The present invention also relates to processes for making milk by harvesting milk from livestock which have been fed such a protein-rich feedstuff. The present invention also relates to processes for making a dairy product from milk harvested from livestock which have been fed such a protein-rich feedstuff. The present invention also relates to processes for making eggs by harvesting eggs from livestock which have been fed such a protein-rich feedstuff. The present invention also relates to processes for making wool or fur by harvesting wool or fur from livestock which have been fed such a protein-rich feedstuff. The present invention also relates to processes for making leather by harvesting skin from livestock which have been fed such a protein-rich feedstuff and converting the skin into leather.

BACKGROUND ART

Feedstuffs are used to feed and raise livestock. Such livestock can be harvested for its meat. Alternatively, livestock can be the source of produce such as eggs and milk, which may be consumed as milk, or converted into another dairy product, such as cheese or yogurt. To produce healthy livestock and increase the yield of produce, it is important for their feed to contain sufficient protein.

Recently, the production of ethanol from corn has become commercially important. In the dry milling (mash distillation) production of ethanol from corn, the process begins by grinding corn into a coarse flour. After the flour is combined with water and/or enzymes to convert the starch to sugar, the product is sterilized and then cooled. After yeast fermentation, ethanol is distilled from the mash. The residual mash is sent to either a centrifuge or screen press to remove as much liquid as possible. The liquid, referred to as corn distillers solubles may be returned to process or sold as a feed additive. The wet distillers grains may also be sold as livestock feed or dried to afford dried distillers grains (DDG).

The DDG is a good source of protein, and it would be desirable to use the DDG as a component of a diet for livestock. However, to make efficient use of DDG in the production of a feed for livestock, the DDG must be dried. Such drying can lead to heat damage of the protein which can, in turn, lead to decreased digestibility of the protein, decreased growth of the livestock, and/or decreased milk production (Non-patent Citation 1 and 2).

Trimethylglycine (also commonly known as TMG or betaine) is an organic compound of the formula $(CH_3)_3N^+CH_2CO_2H$. Trimethylglycine was originally named betaine after its discovery in sugar beets (*Beta vulgaris*) in the 19th century. Betaine occurs widely in nature and its principal physiologic roles have been described as an osmolyte and a methyl donor (Non-patent Citation 3). Betaine is also included in a product which is commercially available as PROTEFERM®. PROTEFERM® is a condensed, extracted glutamic acid fermentation product, and a liquid feed byproduct from the manufacture of monosodium glutamate (MSG).

Patent Citation 1, 2, and 3 disclose a ruminant feed supplement prepared by drying a mixture of glutamic acid fermentation solubles and corn fermentation solubles on a wheat middlings carrier. Patent Citation 4 discloses soil adjuvants prepared in the same way. Corn fermentation solubles are a liquid byproduct of the manufacture of amino acids using corn sugar as a raw material and include very small amounts of protein. Wheat middlings are low in crude protein (17.4 wt. % protein on dry matter basis (Non-patent Citation 4) and not considered a protein-rich feedstuff. Thus, these references do not contain any disclosure of stabilizing the proteins in a protein-rich material during drying.

In addition, PROTEFERM® has been used as an additive to pelletize dried distillers grains with solubles. When added at levels equal to between 5 and 10% on a weight by weight (w/w) basis of dried distillers grains, PROTEFERM® has been able to improve pellet durability and hardness compared with no additive material. The addition of PROTEFERM® to dried distillers grains to equal 10% of the weight is roughly equivalent to adding 1.8 grams of betaine per 100 grams of protein contributed by distillers grains. (This equivalent value can be calculated with the understanding that the betaine content of PROTEFERM® is about 5% and that the crude protein content of dried distillers grains is about 28%. Thus, for example, when PROTEFERM® is present in an amount of 10 wt. % based on dried distillers grains, the equivalent value of betaine is given by [(5% betaine×9.1)/(28% crude protein×90.9)]×100=1.8.). This level of betaine addition is not an effective level to protect protein from heat damage.

Patent Citation 1

U.S. Pat. No. 5,709,894

Patent Citation 2

U.S. Pat. No. 6,514,521

Patent Citation 3

U.S. Pat. No. 6,858,239

Patent Citation 4

U.S. Pat. No. 6,709,481

Non-Patent Citation 1

Nakamura, et al., *J. Anim. Sci.*, vol. 72, pp. 774-782 (1994)

Non-Patent Citation 2

D. H. Kleinschmit, et al., *J. Dairy Sci.*, vol. 90, pp. 2909-2918 (2007)

Non-Patent Citation 3

S. A. Craig, *Am. J. Clin. Nutr.*, vol. 80, pp. 539-549 (2004)

Non-Patent Citation 4

"Nutrient Requirements of Beef Cattle," Table 11-1—Means and Standard Deviations for the Composition of Data of Feeds Commonly Used in Beef Cattle Diets, National Academy Press (1996)

DISCLOSURE OF INVENTION

Technical Problem

Thus, there remains a need for protein-rich feedstuffs which exhibit good digestibility and are resistant to reduction of digestibility as a result of heat damage during drying. There also remains a need for processes for making such feedstuffs, raising livestock by feeding such a protein-rich feedstuff, and making the meat obtained from such livestock.

Accordingly, it is one object of the present invention to provide novel feedstuffs.

It is another object of the present invention to provide novel protein-rich feedstuffs.

It is another object of the present invention to provide novel protein-rich feedstuffs, which are resistant to heat damage during drying.

It is another object of the present invention to provide novel protein-rich feedstuffs which are resistant to reduction of digestibility as a result of heat damage during drying.

It is another object of the present invention to provide novel processes for making such feedstuffs.

It is another object of the present invention to provide novel processes for raising livestock by feeding livestock such a protein-rich feedstuff.

It is another object of the present invention to provide novel processes for making meat by harvesting meat from livestock which have been fed such a protein-rich feedstuff.

It is another object of the present invention to provide novel processes for making milk by harvesting milk from livestock which have been fed such a protein-rich feedstuff.

It is another object of the present invention to provide novel processes for making a dairy product from milk harvested from livestock which have been fed such a protein-rich feedstuff.

It is another object of the present invention to provide novel processes for making eggs or an egg product by harvesting eggs from livestock which have been fed such a protein-rich feedstuff.

It is another object of the present invention to provide novel processes for making wool, fur, or leather by harvesting wool or skin from livestock which have been fed such a protein-rich feedstuff.

These and other objects, which will become apparent during the following detailed description, have been achieved by the inventor's discovery that mixing (a) a protein feed material with (b) either betaine or at least one feed product which contains betaine is effective for stabilizing the resulting protein-rich feedstuff from reduction of digestibility as a result of heat damage during drying.

Technical Solution

Thus, the present invention provides:

1. A protein-rich feedstuff, comprising:
    (a) at least one protein feed material; and
    (b) betaine or at least one feed product which contains betaine;
    wherein:
    the protein-rich feedstuff comprises the betaine in an amount of not less than 3.5 grams of betaine per 100 grams protein in the protein feed material; and
    the protein-rich feedstuff comprises at least 20 wt. % protein on a dry matter basis.

2. A process for making a protein-rich feedstuff, said process comprising:
    (i) mixing (a) at least one protein feed material with (b) betaine or at least one feed product which contains betaine, to obtain a mixture; and
    (ii) drying said mixture, to obtain said protein-rich feedstuff,
    wherein:
    the protein-rich feedstuff comprises the betaine in an amount of not less than 3.5 grams of betaine per 100 grams protein in the protein feed material; and
    the protein-rich feedstuff comprises at least 20 wt. % protein on a dry matter basis.

3. A process for raising livestock, comprising:
    feeding livestock a protein-rich feedstuff, wherein said protein-rich feedstuff comprises:
    (a) at least one protein feed material; and
    (b) betaine or at least one feed product which contains betaine.

4. A process for making meat, comprising:
    feeding livestock a protein-rich feedstuff wherein said protein-rich feedstuff comprises:
    (a) at least one protein feed material; and
    (b) betaine or at least one feed product which contains betaine; and
    harvesting meat from said livestock.

5. A process for making milk, comprising:
    feeding livestock a protein-rich feedstuff wherein said protein-rich feedstuff comprises:
    (a) at least one protein feed material; and
    (b) betaine or at least one feed product which contains betaine; and
    harvesting milk from said livestock.

6. A process for making a dairy product, comprising:
    feeding livestock a protein-rich feedstuff wherein said protein-rich feedstuff comprises:
    (a) at least one protein feed material; and
    (b) betaine or at least one feed product which contains betaine;
    harvesting milk from said livestock; and
    converting said milk into said dairy product.

7. A process for making eggs or an egg product, comprising:
    feeding livestock a protein-rich feedstuff wherein said protein-rich feedstuff comprises:

(a) at least one protein feed material; and
(b) betaine or at least one feed product which contains betaine; and
harvesting eggs from said livestock.

8. A process for making wool, comprising:
feeding livestock a protein-rich feedstuff wherein said protein-rich feedstuff comprises:
(a) at least one protein feed material; and
(b) betaine or at least one feed product which contains betaine; and
harvesting wool from said livestock.

9. A process for making fur, comprising:
feeding livestock a protein-rich feedstuff wherein said protein-rich feedstuff comprises:
(a) at least one protein feed material; and
(b) betaine or at least one feed product which contains betaine; and
harvesting fur from said livestock.

10. A process for making leather, comprising:
feeding livestock a protein-rich feedstuff wherein said protein-rich feedstuff comprises:
(a) at least one protein feed material; and
(b) betaine or at least one feed product which contains betaine;
harvesting skin from said livestock; and
converting said skin into said leather.

Advantageous Effects

According to the invention, a protein-rich feedstuff is provided which exhibit good digestibility and is resistant to reduction of digestibility as a result of heat damage during drying, and a process for making it.

BEST MODE FOR CARRYING OUT THE INVENTION

Thus, in a first embodiment, the present invention provides novel protein-rich feedstuffs comprising (a) at least one protein feed material; and (b) betaine or at least one feed product which contains betaine.

In the context of the present invention, the term "protein feed material" refers to any material which may be used as part of a diet for livestock and contains at least 20 wt. %, preferably at least 24 wt. %, even more preferably at least 28 wt. % protein on a dry matter basis.

Suitable examples of such protein feed materials are distillers grains or any fraction of grains resulting from the industrial production of ethanol. The term "distillers grains" means a coarse grain fraction separated from a whole stillage resulting from the production of ethanol. The production of ethanol may include production of ethanol from, for example, corn, wheat, milo, sorghum, rice, and/or barley. The term "corn distillers grains" means distillers grains when the raw material is corn.

Furthermore, the term "distillers grains plus solubles" is sometimes described "distillers grains with solubles" and means a coarse grain fraction separated from a whole stillage resulting from the production of ethanol with the soluble fraction from the whole stillage which has typically been condensed to reduce total moisture. The term "corn distillers grains plus solubles" means distillers grains plus solubles when the raw material is corn.

Preferred examples of such protein feed materials are corn distillers grains and corn distillers grains plus solubles. In a preferred embodiment, the protein feed material contains grains which are the residue from distillation of ethanol produced by fermentation.

In another embodiment, the protein feed material may be soybean meal, canola meal, corn gluten meal, peanut meal, cottonseed meal, and a mixture thereof. The protein feed material may also be a more refined protein product, such as soy-protein isolate or soy-protein flour. These materials may be obtained as byproducts of oilseed crushing.

In the context of the present invention, the term "betaine" means N, N, N, trimethylglycine which has the formula $(CH_3)_3N^+CH_2CO_2H$. The betaine may be used in the form of neutral zwitterions $((CH_3)_3N^+CH_2CO_2^-)$ or as an addition salt or as a mixture thereof. Alternatively, the betaine may be present as a component of a feed product which contains betaine.

Examples of suitable betaine or at least one feed product which contains betaine include betaine, amino acid fermentation byproduct solubles, molasses containing betaine, condensed separator byproduct, condensed molasses solubles, vinasse, or any mixture thereof. Preferred examples of feed products which contain betaine include a condensed, extracted glutamic acid fermentation product, amino acid fermentation byproduct solubles from the fermentative production lysine, amino acid fermentation byproduct solubles from the fermentative production threonine, or amino acid fermentation byproduct solubles from the fermentative production tryptophan. The condensed, extracted glutamic acid fermentation product is commercially available, for example, as PROTEFERM®.

Typically, the protein feed material and the betaine or feed product which contains betaine are mixed in a ratio such that the amount of betaine is not less than 3.5 grams of betaine per 100 grams of protein in the protein feed material, preferably 3.5 to 12.0 grams of betaine per 100 grams of protein in the protein feed material, even more preferably 4.0 to 8.0 grams of betaine per 100 grams of protein in the protein feed material, still more preferably 4.5 to 6.5 grams of betaine per 100 grams of protein in the protein feed material. When the protein feed material and the betaine or feed product which contains betaine are mixed, it is preferable in a ratio such that the amount of betaine is not less than 4.7 grams of betaine per 100 grams of protein in the protein feed material, more preferably 4.7 to 6.2 grams of betaine per 100 grams of protein in the protein feed material.

In the context of the present invention, the term "protein-rich feedstuff" refers to any feedstuff which may be used as part of a diet for livestock and contains at least 20 wt. %, preferably at least 24 wt. %, and even more preferably at least 28 wt. % protein on a dry matter basis.

The moisture content of the protein-rich feedstuff is typically 0 to 20 wt. %, preferably 0 to 19 wt. %, more preferably 5 to 15 wt. %, and still more preferably 8 to 12 wt. %, based on the total weight of the protein-rich feedstuff.

Of course, the protein-rich feedstuff of the present invention may also contain additional components, so long as they do not have an adverse effect. Examples of such additional components include vitamins, amino acids, preservatives, antibiotics, and any other ingredients conventionally added to feedstuffs. These additional components may be added in amounts conventionally used in feedstuffs.

In another embodiment, the present invention provides processes for making a protein-rich feedstuff, comprising (i) mixing (a) at least one protein feed material with (b) betaine or at least one feed product which contains betaine to obtain a mixture, and (ii) drying the mixture to obtain the protein-rich feedstuff.

The same "protein feed material", "betaine", "feed product which contains betaine", "protein-rich feedstuff", and optional components described above in connection with the protein-rich feedstuff may be used in the processes for making the protein-rich feedstuff.

Typically, the protein feed material will have, at the time it is mixed with the betaine or feed product which contains betaine, a moisture content of 10 to 90 wt. %, preferably 20 to 90 wt %, more preferably 20 to 80 wt. %, and still more preferably 30 to 70 wt. %, based on the total weight of the protein feed material.

The feed product which contains betaine may have a moisture content of 0 to 95 wt. %, preferably 5 to 95 wt. %, more preferably 10 to 75 wt. %, and still more preferably 25 to 65 wt. %, based on the total weight of the feed product which contains betaine.

The mixing may be carried out in any suitable apparatus, such as a paddle mixer, ribbon mixer, plow mixer, v-type mixer, agitator mixer, conical mixer, pan mixer, zig-zag mixer, tumble mixer, or rotary mixer. When the protein feed material or the feed product which contains betaine is mixed in the wet state, the mixing is preferably carried out in a paddle mixer.

The protein feed material and the betaine or feed product which contains betaine are mixed in the same ratios described above in the context of the protein-rich feedstuffs.

When the protein feed material is in a wet state when mixed with the betaine or feed product which contains betaine, or when the feed product which contains betaine is mixed in the wet state, the resulting mixture may then be dried. The drying may be carried out in any suitable apparatus, such as a drum dryer, fluid bed dryer, belt dryer, disc dryer, flush dryer, rotary dryer, rotary vacuum dryer, steam tube dryer, tray dryer, turbo dryer, vacuum dryer or conical dryer. The drying is preferably carried out in a drum dryer.

The drying is suitably carried out by exposing the wet mixture to dry air having a temperature of 80 to 600° C., preferably 150 to 500° C., even more preferably 250 to 450° C., for a time of 1 to 60 minutes, preferably 2 to 30 minutes, even more preferably 4 to 10 minutes. The foregoing drying temperatures and drying times are suitable for commercial production of protein-rich feedstuffs according to the present invention. However, in the processes for making protein-rich feedstuffs according to the present invention, drying can be carried out at temperatures and for times outside of the ranges enumerated above. For example, when preparing smaller batches, as in the case of the Examples described herein, it may be desirable to employ lower drying temperatures and longer drying times.

Typically, the resulting dried protein-rich feedstuff will have a final moisture content of 0 to 20 wt. %, preferably 0 to 19 wt. %, more preferably 5 to 15 wt. %, still more preferably 8 to 12 wt. %, based on the total weight of the protein-rich feedstuff.

As shown in the Examples below, the addition of betaine or a feed product which contains betaine to a protein feed material serves to protect the protein from heat degradation during the drying process such that the deterioration of the digestibility of the protein is inhibited.

A protein-rich feedstuff is obtainable by process comprising: (i) mixing (a) at least one protein feed material with (b) betaine or at least one feed product which contains betaine, to obtain a mixture; and (ii) drying said mixture, to obtain said protein-rich feedstuff, wherein: the protein-rich feedstuff comprises the betaine in an amount of not less than 3.5 grams of betaine per 100 grams protein in the protein feed material; and the protein-rich feedstuff comprises at least 20 wt. % protein on a dry matter basis.

In another embodiment, present invention provides novel processes for raising livestock by feeding livestock such a protein-rich feedstuff. Such livestock includes cattle, oxen, bison, deer, pigs, goats, sheep, lambs, rabbits, lama, alpaca, foxes, mink, ermine, weasel, stoat, chinchilla, beavers, sables, otters, kangaroos, yaks, and fowl or poultry (including chickens, turkeys, ducks, game hens, ostrich, emu, and pheasants) and fish (including salmon, catfish, etc) and reptiles (including alligators, crocodiles, lizards, snakes, etc.). In exemplary embodiments, livestock includes ruminant animals.

These livestock may be fed the protein-rich feedstuff of the present invention at any time and in any amount during their life. That is, the livestock may be fed the feedstuff of the present invention either by itself or as part of a diet which includes other feedstuffs. Moreover, the livestock may be fed the protein-rich feedstuff of the present invention at any time during their lifetime. The livestock may be fed the protein-rich feedstuff of the present invention continuously, at regular intervals, or intermittently. The livestock may be fed the protein-rich feedstuff of the present invention in an amount such that it accounts for all, a majority, or a minority of the protein in the livestock's diet for any portion of time in the animal's life. Preferably, the livestock is fed the protein-rich feedstock of the present invention in an amount such that it accounts for a majority of the protein in the animal's diet for a significant portion of the animal's lifetime.

In another embodiment, the present invention provides novel processes for making meat by harvesting meat from livestock which have been fed such a protein-rich feedstuff. The livestock in this embodiment are the same as those described above in connection with the present process for raising livestock. The feeding may be carried out as described above in connection with the process for raising livestock.

The meat may be harvesting at any suitable time during the animal's lifetime. The harvesting of the meat may be carried out using the techniques conventional in the art of butchering. Typical meats to be harvested include, beef, pork, mutton, lamb, venison, bison, rabbit, chicken, turkey, duck, ostrich, emu, pheasant, etc. The meat may be sold fresh or frozen. The meat may be processed as described in Kirk-Othmer, *Encyclopedia of Chemical Technology*, Fourth Ed., Wiley-Interscience, NY, vol. 16, pp. 68-87, 1995, which is incorporated herein by reference.

In another embodiment, the present invention provides novel processes for making milk by harvesting milk from livestock which have been fed such a protein-rich feedstuff. The livestock in this embodiment are those which produce milk, such as cattle, oxen, bison, deer, pigs, goats, sheep, etc. The feeding may be carried out as described above in connection with the process for raising livestock. The harvesting of the milk may be carried out using the conventional techniques known to those in the art. The milk may be processed, stored, cooled, shipped, and packaged, as described in Kirk-Othmer, *Encyclopedia of Chemical Technology*, Fourth Ed., Wiley-Interscience, NY, vol. 16, pp. 700-746, 1995, which is incorporated herein by reference.

In another embodiment, the present invention provides processes for making a dairy product from the milk harvested from an animal which has been fed the protein-rich feedstuff of the present invention. Such dairy products include evaporated and condensed milk, dry milk, cream, anhydrous milk fat, butter, buttermilk, cheese, yogurt, and frozen desserts (such as ice cream, frozen yogurt, ice milk, sherbets, and mellorine), lactose, and casein. The conversion of the milk into the dairy product may be carried out using conventional techniques known to those skilled in the art as described in Kirk-Othmer, *Encyclopedia of Chemical Technology*, Fourth Ed., Wiley-Interscience, NY, vol. 16, pp. 700-746, 1995, which is incorporated herein by reference.

In another embodiment, the present invention provides novel processes for making eggs or an egg product by harvesting eggs from livestock which have been fed such a protein-rich feedstuff. The livestock in this embodiment are those which produce eggs, such as chickens, turkeys, ducks, game hens, ostrich, emu, pheasants, etc. The feeding may be carried out as described above in connection with the process for raising livestock. The egg products include liquid egg products (such as egg white, egg yolk, whole egg, extended shelf life refrigerated liquid egg products, and concentrated sugared whole egg), frozen egg products (such as egg white, plain whole egg, whole egg with yolk added, plain egg yolk, fortified whole egg with corn syrup, sugared egg yolk, salted egg yolk, salted whole egg, and scrambled eggs and omelets), and dried egg products (such as dried egg white, dried whole egg, and dried egg yolk). The production of the eggs and the egg products may be carried out using the conventional techniques known to those in the art as described in Kirk-Othmer, *Encyclopedia of Chemical Technology*, Fourth Ed., Wiley-Interscience, NY, vol. 18, pp. 887-905, 1993, which is incorporated herein by reference.

In another embodiment, the present invention provides novel processes for making wool by harvesting wool from livestock which have been fed such a protein-rich feedstuff. The livestock in this embodiment are those which produce wool, such as goats, sheep, lambs, lama, alpaca, etc. The feeding may be carried out as described above in connection with the process for raising livestock. The wool may be harvested and treated by conventional techniques known to those skill in the art and as described in Kirk-Othmer, *Encyclopedia of Chemical Technology*, Fourth Ed., Wiley-Interscience, NY, vol. 25, pp. 664-712, 1998, which is incorporated herein by reference.

In another embodiment, the present invention provides novel processes for making fur by harvesting fur from livestock which have been fed such a protein-rich feedstuff. The livestock in this embodiment are those which produce fur, such as rabbits, lama, alpaca, foxes, mink, ermine, weasel, stoat, chinchilla, beavers, sables, otters, etc. The feeding may be carried out as described above in connection with the process for raising livestock. The fur may be harvested and treated by conventional techniques known to those skill in the art and as described in Kirk-Othmer, *Encyclopedia of Chemical Technology*, Fourth Ed., Wiley-Interscience, NY, vol. 15, pp. 159-177, 1995, which is incorporated herein by reference.

In another embodiment, the present invention provides novel processes for making leather by harvesting skin from livestock which have been fed such a protein-rich feedstuff and converting the skin into leather. In the context of the present invention, the term leather also includes suede and the term skin include hides and pelts. The livestock in this embodiment are those whose skin may be converted into leather, such as cattle, oxen, bison, deer, pigs, goats, sheep, lambs, rabbits, lama, alpaca, foxes, mink, ermine, weasel, stoat, kangaroos, yaks, chinchilla, ostrich, emu, alligators, crocodiles, lizards, snakes, etc. The feeding may be carried out as described above in connection with the process for raising livestock. The skin may be harvested and converted into leather by conventional techniques known to those skill in the art and as described in Kirk-Othmer, *Encyclopedia of Chemical Technology*, Fourth Ed., Wiley-Interscience, NY, vol. 15, pp. 159-177, 1995, which is incorporated herein by reference.

Other features of the invention will become apparent in the course of the following descriptions of exemplary embodiments which are given for illustration of the invention and are not intended to be limiting thereof.

EXAMPLES

Example 1

The objective of this Example was to evaluate the effect of PROTEFERM® and heat upon protein digestibility in corn distillers grains plus solubles ("DGS"). A sample of wet DGS was obtained locally. A 2×2 factorial experiment was designed that included PROTEFERM® added to wet DGS at either 0 or 15% of the weight of wet DGS, as is (0 or 9.4% dry basis), and then heated at either 50° C. or 140° C. in a forced air oven for 4 hours followed by drying at 30° C. The moisture content of the wet DGS was determined as 41.9% of the total weight by loss on drying. PROTEFERM® contains 60% moisture. All treatments were applied in triplicate. After drying, total Kjeldahl nitrogen (TKN) and ammonia nitrogen (AN) of samples was determined respectively. Soluble ammonia nitrogen was determined by stirring 1.5 g of sample in 100 ml of deionized water for 1 hour and measuring the ammonia nitrogen content of the supernatant by distillation with sodium hydroxide. The water insoluble feed was filtered, rinsed and dried gently at 30° C. in a forced air oven. Kjeldahl nitrogen was determined on the rinsed and dried samples. Using the rinsed samples, intestinal protein digestibility was estimated using the method described by Calsamiglia and Stern (see, *J. Anim. Sci., vol.* 73, pp. 1459-1465 (1995)). Briefly, 15 mg of nitrogen from each sample was digested in-vitro (in replicates of six) with 10 ml of pepsin solution containing 1 g/L pepsin (Sigma P-7012) adjusted to pH 1.9 for one hour. Pepsin digestion was stopped by adding 0.5 ml 1N NaOH and then 13.5 ml of pancreatin solution containing 0.5M $KH_2PO_4$, 3 g/L pancreatin (Sigma P-7545) and 50 mg/L thymol for 24 hours of digestion. At the end of the digestion period, trichloroacetic acid (3 ml) was added to each tube to stop digestion and to precipitate proteins and large peptides. The tubes were centrifuged (3,200×g) and the supernatant was analyzed for total nitrogen. Three blanks were included in each run. Protein digestibility of the feed was calculated as the mg of nitrogen in the digest supernatent divided by the original mg of nitrogen in each tube at the start of digestion.

The ammonia nitrogen content was expectedly higher in DGS+ PROTEFERM® as PROTEFERM® contains approximately 12% ammonia nitrogen on a dry basis (see, Table 2). Dried distillers grains also contain non-protein nitrogen because urea is commonly added to the fermentation media during the production of ethanol. In this trial, approximately 11% of the total nitrogen in DGS was ammonium nitrogen. Surprisingly, the ammonia nitrogen in DGS was largely insoluble in water, approximately 94% of the total ammonia nitrogen, and drying temperature had no effect. The insoluble ammonia nitrogen was similar between DGS and DGS+ PROTEFERM®, indicating that rinsing was effective in removing all the ammonia nitrogen in DGS+ PROTEFERM® added by PROTEFERM® (ammonium chloride). The total nitrogen content of rinsed samples was similar between DGS and DGS+ PROTEFERM®, with no apparent effect of temperature.

The results of enzyme digestion of the rinsed samples are shown in Table 3. The data show a significant interaction between PROTEFERM® level and heat treatment. As expected, high heat treatment at 140° C., decreased the digestibility of protein in DGS compared with mild heating, 50° C. However, DGS+ PROTEFERM® did not exhibit a decrease in protein digestibility with high heat treatment versus low heat and was similar to DGS with low heat.

TABLE 1

Typical composition of dried distillers grains plus solubles (dried DGS).

| Item | Typical result |
|---|---|
| Dry matter | 90.0 |
| Crude protein, % of dry matter | 30.0 |
| Fat, % of dry matter | 10.0 |
| Fiber, % of dry matter | 7.0 |
| Potassium, % of dry matter | 1.2 |
| Sodium, % of dry matter | 0.2 |
| Sulfur, % of dry matter | 0.6 |
| Chlorine, % of dry matter | 0.1 |
| Lysine, % of dry matter | 1.0 |
| Threonine, % of dry matter | 1.2 |
| Tryptophan, % of dry matter | 0.2 |

TABLE 2

Nitrogen Content of Samples and Soluble Nitrogen.

| | Treatment | | | |
|---|---|---|---|---|
| | DGS | | DGS + PROTEFERM® | |
| | Drying Temperature (° C.) | | | |
| | 50 | 140 | 50 | 140 |
| TKN, % of dry matter | 4.78 | 4.80 | 5.94 | 6.10 |
| Total AN, % of dry matter | 0.54 | 0.56 | 1.66 | 1.68 |
| Insoluble AN, % of dry matter | 0.51 | 0.53 | 0.46 | 0.48 |
| Soluble AN, % of total AN | 5.02 | 5.49 | 72.33 | 71.29 |
| TKN of rinsed samples, % of dry matter | 5.16 | 5.06 | 5.16 | 5.26 |

TKN: total Kjeldahl nitrogen,
AN: ammonia nitrogen

TABLE 3

Digestibility of Water-Insoluble Protein in Corn distillers Grains Dried at High or Low Temperature with and without PROTEFERM®. g/100 g.

| | PROTEFERM® | |
|---|---|---|
| Temperature (° C.) | − | + |
| 50 | 48.1 | 47.2 |
| 140 | 41.2 | 48.3 |

Main effect of PROTEFERM® P = 0.13.
Main effect of Temperature P = 0.15.
Interaction P = 0.05.
SEM (Standard Error of the Mean) = 1.45

Example 2

The objective of this Example was to evaluate the effect of heating interval upon the digestibility of DGS with added PROTEFERM® or not. In this Example, the same DGS was used as in Example 1 after being stored frozen. PROTEFERM® was added to wet DGS to equal 15% of the weight of wet DGS, as is (9.4%, dry basis). Treated and untreated wet DGS was weighed into aluminum pans (c.a. 150 g) and placed into a 140° C. forced air oven for 0.25, 0.5, 1.0, 2.0, and 4.0 hours in triplicate for each time interval. After treating samples with high temperature, they were allowed to dry completely at a low temperature (30° C.). The dried samples were composited within treatment for analyses. Water soluble protein and enzyme digestibility of water insoluble protein was determined for each sample as in Example 1.

Although the treatments were heat treated in triplicate, the dried samples were composited for analyses. For this reason, statistical comparisons could not be made. Treatment variation was thought to occur during the heat-treatment step, so an effort was made to replicate samples during this step. Heating did not effect soluble nitrogen in DGS until 4 hours when it was reduced by 32% compared with 15 minutes (see, Table 4). Soluble nitrogen was not reduced in DGS+ PROTEFERM® after heating and soluble AN was not affected by heating for either treatment. Total N was similar between rinsed samples of DGS and DGS+ PROTEFERM® at all heating intervals, indicating that all of the soluble N provided by PROTEFERM® was removed by rinsing. The enzymatic digestion of insoluble protein nitrogen in DGS was reduced after 1 hour of heating at 140° C. compared with 15 minutes (see, Table 5). The protein digestion was reduced even further at 4 hours of heating. Heating up to 4 hours did not have any apparent affect upon the enzymatic digestion of protein nitrogen in DGS+ PROTEFERM®, and the digestion of protein nitrogen in DGS+ PROTEFERM® was similar to DGS with only 15 minutes of heating. The DGS+ PROTEFERM® 15 minutes sample had a low digestibility compared with all other times.

TABLE 4

Nitrogen content of samples and soluble nitrogen.

| | Heating interval at 140° C. (hours) | | | | |
|---|---|---|---|---|---|
| | .25 | .50 | 1.0 | 2.0 | 4.0 |
| TKN, % of dry matter | | | | | |
| DGS | 4.56 | 4.52 | 4.55 | 4.52 | 4.50 |
| DGS + PROTEFERM® | 5.66 | 5.69 | 5.61 | 5.58 | 5.60 |
| Soluble N, % of dry matter | | | | | |
| DGS | 0.53 | 0.55 | 0.51 | 0.55 | 0.36 |
| DGS + PROTEFERM® | 1.88 | 1.74 | 1.90 | 1.63 | 1.75 |
| Soluble AN, % of dry matter | | | | | |
| DGS | 0.07 | 0.09 | nd | nd | 0.06 |
| DGS + PROTEFERM® | 1.14 | 1.12 | 1.10 | 0.98 | 1.02 |
| TKN rinsed samples, % of dry matter | | | | | |
| DGS | 4.81 | 4.80 | 4.80 | 4.70 | 5.07 |
| DGS + PROTEFERM® | 4.97 | 4.91 | 4.87 | 5.11 | 5.00 | nd: Not determined,
soluble N: soluble nitrogen

TABLE 5

Enzymatic digestion of protein in corn distillers grains dried at 140° C. with PROTEFERM® or not for various lengths of time. g/100 g.

| | Time (hours) | | | | |
|---|---|---|---|---|---|
| | .25 | .50 | 1.0 | 2.0 | 4.0 |
| Distillers Grains | 48.7 | 48.0 | 43.2 | 44.9 | 39.8 |
| Distillers Grains + PROTEFERM® | 43.1 | 49.4 | 50.4 | 48.3 | 49.5 |

Example 3

The objective of this Example was to evaluate the effect of drying DGS with different levels of added PROTEFERM® or ammonium chloride upon the protein digestibility of DGS. To wet DGS (the wet DGS contains 41.9% moisture as shown in Example 1), PROTEFERM® was added to equal 0, 5, 10, 15 and 20% and $NH_4Cl$ (in 20% solution) to equal 4% of the weight of wet DGS. The $NH_4Cl$ treatment and the 20% PROTEFERM® treatment provided an equal amount of $NH_4Cl$. (When PROTEFERM® is present in amounts of 0, 5, 10, 15 and 20 wt. % based on wet DGS, the equivalent values of betaine are 0, 1.6, 3.1, 4.7 and 6.2 grams of betaine per 100 grams of protein contributed by wet distillers grains, respectively. For example, when PROTEFERM® is present in an amount of 10 wt. % based on wet distillers grains, the equivalent value of betaine is given by [(5% betaine×9.1)/(28% crude protein×90.9×0.581)]× 100=3.1.). The samples were mixed thoroughly and weighed (c.a. 150 g) into aluminum trays in replicates of four. These trays were placed into a forced air oven set at 140° C. for 4 hours. After 4 hours, the samples were removed and dried completely at low temperature (30° C.). In addition, wet DGS was dried in quadruplicate trays at low temperature without high heat treatment as a negative control. Water soluble protein and enzyme digestibility of water insoluble protein was determined for each sample as in Example 1.

The total nitrogen of the rinsed samples was similar among treatments that were heat treated. The negative control, which was dried only at low temperature, had numerically lower nitrogen content. This difference may be explained by the loss of volatiles during the high heat treatment as well as by nitrogen being bound into an insoluble form during heat treatment. The nitrogen content of samples and soluble nitrogen are shown in Table 6. The enzyme digestibility of each sample is shown in Table 7. In this trial, there were no statistical differences (P>0.05) among treatments; however, there was a numerical reduction in protein digestibility due to heat damage (54.1 vs. 60.6%) in this trial which agrees with the results of the previous two trials. There also seemed to be trend for higher levels of PROTEFERM® to attenuate the reduction in protein digestibility due to heating while lower levels had no effect. These data suggest the amount of PROTEFERM® needed to protect protein from heat damage is more than 10% (for example, 15%, 20%) of the weight of DGS as is.

TABLE 6

Nitrogen Content of samples and soluble nitrogen.

| | Treatments | | | | | | |
|---|---|---|---|---|---|---|---|
| Item | Neg. Control | 0% Prot. | 5% Prot. | 10% Prot. | 15% Prot. | 20% Prot. | 4% $NH_4Cl$ |
| TKN, % of dry matter | 4.98 | 4.82 | 5.25 | 5.95 | 6.36 | 6.58 | 6.56 |
| Total AN, % of dry matter | 0.59 | 0.60 | 0.99 | 1.39 | 1.75 | 2.03 | 2.19 |
| Insoluble AN, % of dry matter | 0.45 | 0.43 | 0.37 | 0.45 | 0.38 | 0.30 | 0.42 |
| Soluble AN, % of total AN | 23.93 | 30.10 | 62.67 | 67.59 | 78.43 | 85.13 | 80.62 |

TABLE 6-continued

Nitrogen Content of samples and soluble nitrogen.

| | Treatments | | | | | | |
|---|---|---|---|---|---|---|---|
| Item | Neg. Control | 0% Prot. | 5% Prot. | 10% Prot. | 15% Prot. | 20% Prot. | 4% $NH_4Cl$ |
| TKN of rinsed samples, % of dry matter | 4.67 | 5.10 | 5.28 | 5.27 | 5.19 | 5.19 | 5.08 |

Prot.: PROTEFERM ®;
10% Prot.: PROTEFERM ® is 10 wt. % of wet DGS

TABLE 7

Enzymatic digestion of protein of corn distillers grains dried with various amounts of PROTEFERM ® added or ammonium chloride. g/100 g.

| Drying Temperature | | | | | | | |
|---|---|---|---|---|---|---|---|
| 30° C. | 140° C. | | | | | | |
| 0% Prot. | 0% Prot. | 5% Prot. | 10% Prot. | 15% Prot. | 20% Prot. | 4% $NH_4Cl$ | SEM |
| 60.6 | 54.1 | 54.1 | 54.4 | 58.5 | 57.3 | 53.4 | 2.02 |

Prot.: PROTEFERM ®;
10% Prot.: PROTEFERM ® is 10 wt. % of wet DGS

Example 4

The objective of this Example was to determine the effect that individual, major components of PROTEFERM® have upon the digestibility of protein in DGS when subjected to heat treatment. The three previous Examples have shown the beneficial effect of PROTEFERM® to protect DGS protein digestibility from heat damage when added to equal more than 10% (for example, 15%, 20%) of the weight of DGS on an as is basis. In the current trial, DGS was mixed with either of the components, PROTEFERM®, ammonium chloride, betaine, glutamic acid or lactic acid at the ratios listed in Table 8 before heat treating at 140° C. for 4 hours in replicates of four using covered aluminum trays containing approximately 150 g per tray. After heat treating, uncovered trays, along with a negative control of wet DGS in quadruplicate, were dried at low temperature (30° C.). Water soluble protein and enzyme digestibility of water insoluble protein was determined for each sample as in Example 1. Differences among treatment means were determined by the general linear model of analyses of variance.

Heating wet DGS significantly reduced digestibility of water insoluble protein compared with control DGS dried at low temperature (see, Table 10). In this trial, the digestibility of water insoluble protein in DGS+ PROTEFERM® was intermediate between the control and heat treated DGS and tended to be higher compared with heat treated DGS, P=0.07. Glutamic acid, lactic acid, and ammonium chloride all had protein digestibility similar to dried DGS and significantly lower compared with the control. On the other hand, betaine was similar in protein digestibility to the control and significantly higher as compared with heat treated DGS. The nitrogen content of the negative control after rinsing was lower compared with all heat treated samples (see, Table 9). The nitrogen contents of all rinsed and heat treated samples were similar except PROTE- FERM® and ammonium chloride tend to be a little higher. Based upon the results of Examples 1-3, there is no reason to expect this.

TABLE 8

Treatments Applied to DGS before Heat Treatment.

| Treatment component | g component added/ 100 g of wet DGS | g extra water added/ 100 g of wet DGS |
|---|---|---|
| PROTEFERM ® | 20.0 | 0 |
| Ammonium Chloride ($NH_4Cl$) | 4.0 | 12.0 |
| Betaine | 1.0 | 12.0 |
| Glutamic acid | 1.0 | 12.0 |
| Lactic acid | 1.0 | 12.0 |

TABLE 9

Nitrogen Content of Samples and Soluble Nitrogen.

| | Treatment | | | | | | |
|---|---|---|---|---|---|---|---|
| Item | Negative Control | dried DGS | PROTEFERM ® | $NH_4Cl$ | Betaine | Glutamic acid | Lactic acid |
| TKN, % of dry matter | 4.28 | 4.30 | 5.49 | 5.48 | 4.40 | 4.41 | 4.27 |
| TKN of rinsed samples, % of dry matter | 5.22 | 5.43 | 5.72 | 5.65 | 5.36 | 5.41 | 5.28 |
| Soluble AN, % of dry matter | 0.00 | 0.00 | 0.85 | 1.29 | 0.00 | 0.00 | 0.01 |
| Soluble TKN, % of dry matter | 0.39 | 0.44 | 1.86 | 1.74 | 0.55 | 0.59 | 0.44 |

TABLE 10

Enzymatic digestion of protein in corn distillers grains treated with various compounds and dried at high temperature or low temperature control. g/100 g.

| Treatment | | | | | | | |
|---|---|---|---|---|---|---|---|
| Negative Control | dried DGS | PROTEFERM ® | $NH_4Cl$ | Betaine | Glutamic acid | Lactic acid | SEM |
| $69.85^a$ | $60.14^b$ | $65.00^{ab}$ | $64.20^{bc}$ | $67.13^{ac}$ | $63.34^b$ | $61.80^b$ | 1.17 |

$^{abc}$Means within row with unlike superscripts differ, P < 0.05.

Example 5

The effectiveness of betaine in protecting soybean (*Glycine max*) protein from heat damage is evaluated. Soy-protein isolate containing 90% protein is obtained. A 2×6 factorial experiment is carried out to evaluate enzymatic digestibility of soy-protein isolate after heating at 140° C. for 0.0, 0.5, 1.0, 2.0, 3.0 or 4.0 hours both with and without added betaine. 36 samples are prepared. 18 of the samples include 36 g of a water solution containing 20% betaine added to 200 g of soy-protein isolate, so that each of the 18 samples includes 4 g betaine per 100 g soy-protein. The other 18 samples include 36 g of a water solution containing 0% betaine added to 200 g of soy-protein isolate, so that each of the 18 samples includes 0 g betaine per 100 g soy-protein. Accordingly, three betaine-containing samples and three betaine-free examples are prepared for each heat treatment period. The samples are placed into aluminum trays, covered with foil, and placed into a pre-heated, forced air oven set at 140° C. Samples are removed after each heat period elapses and uncovered and allowed to cool. After all samples are heat treated and cooled, the samples are dried completely at a temperature of 30° C. The samples are ground sufficiently to pass through a 1 mm screen. Total Kjeldahl nitrogen is determined and enzyme digestibility of each sample is measured using the pepsin-pancreatin method described in Example 1.

Example 6

The effectiveness of betaine in protecting soybean (*Glycine max*) protein from heat damage is evaluated. Soy-protein flour containing 50% protein is obtained. A 2×6 factorial experiment is carried out to evaluate enzymatic digestibility of soy-protein flour after heating at 140° C. for 0.0, 0.5, 1.0, 2.0, 3.0 or 4.0 hours both with and without added betaine. 36 samples are prepared. 18 of the samples include 20 g of a water solution containing 20% betaine added to 200 g of soy-protein flour, so that each of the 18 samples includes 4 g betaine per 100 g soy-protein. The other 18 samples include 20 g of a water solution containing 0% betaine added to 200 g of soy-protein flour, so that each of the 18 samples includes 0 g betaine per 100 g soy-protein. Accordingly, three betaine-containing samples and three betaine-free examples are prepared for each heat treatment period. The samples are placed into aluminum trays, covered with foil, and placed into a pre-heated, forced air oven set at 140° C. Samples are removed after each heat period elapses and uncovered and allowed to cool. After all samples are heat treated and cooled, the samples are dried completely at a temperature of 30° C. The samples are ground sufficiently to pass through a 1 mm screen. Total Kjeldahl nitrogen is determined and enzyme digestibility of each sample is measured using the pepsin-pancreatin method described in Example 1.

Example 7

The amount of betaine required to effectively protect soybean (*Glycine max*) protein from heat damage is evaluated. Soy-protein isolate containing 90% protein is obtained. 12 samples are prepared. 3 of the samples include 36 g of a water solution containing 0% betaine added to 200 g of soy-protein isolate, so that each of the 3 samples includes 0 g betaine per 100 g soy-protein. 3 of the samples include 36 g of a water solution containing 10% betaine added to 200 g of soy-protein isolate, so that each of the 3 samples includes 2 g betaine per 100 g soy-protein. 3 of the samples include 36 g of a water solution containing 20% betaine added to 200 g of soy-protein isolate, so that each of the 3 samples includes 4 g betaine per 100 g soy-protein. 3 of the samples include 36 g of a water solution containing 40% betaine added to 200 g of soy-protein isolate, so that each of the 3 samples includes 8 g betaine per 100 g soy-protein. The samples are placed into aluminum trays, covered with foil, and placed into a pre-heated, forced air oven set at 140° C. The samples are removed after a period of 180 minutes elapses and uncovered and allowed to cool. After the samples are heat treated and cooled, the samples are dried completely at a temperature of 30° C. Dried samples are ground to pass a 1 mm screen. Total Kjeldahl nitrogen is determined and enzyme digestibility of each sample is measured by the pepsin-pancreatin method described in Example 1.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

INDUSTRIAL APPLICABILITY

The protein-rich feedstuff, the process of making it, the process for raising livestock and the processes for making products from the livestock are applicable to manufacturing feedstuffs for livestock, to raising livestock and to making products from the livestock.

The invention claimed is:
1. A process of making a protein-containing feedstuff, said process comprising:
(i) mixing (a) at least one protein feed material with (b) betaine or at least one feed product which contains betaine, to obtain a mixture; and
(ii) drying said mixture, to obtain said protein-containing feedstuff,
wherein:
said drying is conducted with heating, and
said protein-containing feedstuff comprises at least 20 wt. % protein on a dry matter basis, and
said protein-containing feedstuff has a moisture content between 0 and 20 wt. %, based on the total weight of said protein-containing feedstuff,
wherein said (a) protein feed material and said (b) betaine or at least one feed product which contains betaine are mixed in relative amounts such that a ratio of betaine to protein in said protein feed material is 1.6 to 12 grams of betaine to 100 grams of protein in said protein feed material.

2. A process according to claim 1, wherein said at least one protein feed material is distillers grains or any fraction of grains resulting from industrial production of ethanol.

3. A process according to claim 2, wherein said grains are grains resulting from industrial production of ethanol from corn, wheat, milo, sorghum, rice or barley.

4. A process according to claim 1, wherein said at least one protein feed material comprises corn distillers grains.

5. A process according to claim 1, wherein said at least one protein feed material comprises corn distillers grains plus solubles.

6. A process according to claim 1, wherein said at least one protein feed material comprises at least one material selected from the group consisting of soybean meal, soy-protein flour, soy-protein isolate, canola meal, corn gluten meal, peanut meal, and cottonseed meal.

7. A process according to claim 1, wherein said betaine or at least one feed product which contains betaine is any one of betaine, amino acid fermentation byproduct solubles, molasses containing betaine, condensed separator byproduct, condensed molasses solubles, vinasse, and a mixture thereof.

8. A process according to claim 1, wherein said at least one feed product which contains betaine is selected from the group consisting of a condensed, extracted glutamic acid fermentation product, amino acid fermentation byproduct solubles from the fermentative production lysine, amino acid fermentation byproduct solubles from the fermentative production threonine, and amino acid fermentation byproduct solubles from the fermentative production tryptophan.

9. A process according to claim 1, wherein said at least one feed product which contains betaine comprises a condensed, extracted glutamic acid fermentation product.

10. A process according to claim 1, wherein said at least one feed product which contains betaine is amino acid fermentation byproduct solubles from the fermentative production lysine.

11. A process according to claim 1, wherein said protein feed material has a moisture content between 10 and 90 wt. %, based on the total weight of said protein feed material.

12. A process according to claim 1, wherein said betaine or at least one feed product which contains betaine has a moisture content between 0 and 95 wt. %, based on the total weight of said betaine or at least one feed product which contains betaine.

13. A process according to claim 1, wherein said drying comprises exposing said mixture to an atmosphere having a temperature of 80 to 600° C.

14. A process according to claim 1, wherein said drying comprises exposing said mixture to an atmosphere having a temperature of 80 to 600° C. for a time of 1 to 60 minutes.

15. A process according to claim 1, wherein said drying comprises exposing said mixture to an atmosphere having a temperature of 80 to 250° C.

16. A process according to claim 1, wherein said drying comprises exposing said mixture to an atmosphere having a temperature of 80 to 150° C.

17. A process according to claim 1, wherein said drying comprises exposing said mixture to an atmosphere having a temperature of 150 to 250° C.

18. A process according to claim 1, wherein said protein-containing feedstuff has a moisture content of 0 to 19 wt. %, based on the total weight of said protein-containing feedstuff.

19. A process according to claim 1, wherein said (a) protein feed material and said (b) betaine or at least one feed product which contains betaine are mixed in relative amounts such that a ratio of betaine to protein in said protein feed material is 1.6 to 8 grams of betaine to 100 grams of protein in said protein feed material.

* * * * *